United States Patent
Colditz

(10) Patent No.: US 12,251,328 B2
(45) Date of Patent: Mar. 18, 2025

(54) WRIST BRACE STRAP

(71) Applicant: Judy Carol Colditz, Raleigh, NC (US)

(72) Inventor: Judy Carol Colditz, Raleigh, NC (US)

(73) Assignee: JUDY CAROL COLDITZ REVOCABLE TRUST, Raleigh, NC (US)

(*) Notice: Subject to any disclaimer, the term of this patent is extended or adjusted under 35 U.S.C. 154(b) by 113 days.

(21) Appl. No.: 17/382,684

(22) Filed: Jul. 22, 2021

(65) Prior Publication Data

US 2022/0023083 A1  Jan. 27, 2022

Related U.S. Application Data

(60) Provisional application No. 63/055,576, filed on Jul. 23, 2020.

(51) Int. Cl.
*A61F 5/01* (2006.01)

(52) U.S. Cl.
CPC .................. *A61F 5/0118* (2013.01)

(58) Field of Classification Search
CPC .... A61F 5/05866; A61F 5/013; A61F 5/0118; A61F 13/107; A61F 5/3723; A61F 5/05858; A61F 5/01; A61F 5/0102; A61F 13/108; A61F 5/32; A61F 5/30; A61F 5/3776; Y10S 2/917; Y10S 2/91; A41D 19/0089; A41D 20/00; A41D 19/01; A41D 13/088; A41D 13/081; A41D 13/082; A41D 2400/32; A61H 1/008; A61H 2201/1635; A61H 7/001; A61G 13/1235
USPC .......................................................... 602/21
See application file for complete search history.

(56) References Cited

U.S. PATENT DOCUMENTS

| | | | | | |
|---|---|---|---|---|---|
| 2,506,804 | A | * | 5/1950 | Martin | A41C 1/08 |
| | | | | | D2/702 |
| 2,745,580 | A | * | 5/1956 | Ward | G04B 37/005 |
| | | | | | 368/286 |
| 4,881,533 | A | | 11/1989 | Teurlings | |
| 5,020,521 | A | * | 6/1991 | Salort | A61F 5/0118 |
| | | | | | 602/20 |
| 5,152,302 | A | * | 10/1992 | Fareed | A61F 5/34 |
| | | | | | 128/DIG. 20 |

(Continued)

FOREIGN PATENT DOCUMENTS

WO        9900076 A1    1/1999
WO   WO-2018102521 A1 *  6/2018  ............... A61F 5/01

OTHER PUBLICATIONS

International Search Report and Written Opinion for PCT/US2021/042721 mailed Nov. 4, 2021, 11 pages.

*Primary Examiner* — Ophelia A Hawthorne
*Assistant Examiner* — Michael Milo
(74) *Attorney, Agent, or Firm* — Myers Bigel, P.A.

(57) ABSTRACT

A wrist brace for providing support to carpal bones within the wrist includes an elongated strap sized and configured to encircle a wrist; a first bracing member on the strap and configured for positioning on a volar side of a wrist; and a second bracing member spaced apart from the first bracing member on the strap and configured for positioning on the dorsal side of a wrist; wherein the first and second bracing members extend outward from the elongated strap and have a surface area that, together with the elongated strap, supports the carpal bones within the wrist.

24 Claims, 13 Drawing Sheets

(56) References Cited

U.S. PATENT DOCUMENTS

| | | | |
|---|---|---|---|
| 5,642,739 A * | 7/1997 | Fareed | A61N 2/06 |
| | | | 600/15 |
| 5,652,955 A * | 8/1997 | Skewis | A61F 5/0118 |
| | | | 2/16 |
| 5,672,150 A | 9/1997 | Cox | |
| 8,398,573 B2 | 3/2013 | Howard | |
| 2002/0007134 A1 * | 1/2002 | Bracamonte-Sommer | A61F 5/05866 |
| | | | 602/5 |
| 2002/0062095 A1 | 5/2002 | Slautterback | |
| 2008/0071205 A1 * | 3/2008 | Howard | A61F 5/0118 |
| | | | 602/21 |
| 2009/0131842 A1 * | 5/2009 | Rodgers, Jr. | G06Q 30/0601 |
| | | | 705/26.1 |
| 2009/0171257 A1 * | 7/2009 | Centen | A61F 5/0118 |
| | | | 602/21 |
| 2011/0166635 A1 * | 7/2011 | Nelson | A61F 7/02 |
| | | | 607/112 |
| 2013/0283640 A1 | 10/2013 | Elder et al. | |
| 2017/0156966 A1 * | 6/2017 | Chung | A61H 7/001 |
| 2019/0357661 A1 * | 11/2019 | Walters, Jr. | A45F 5/00 |

* cited by examiner

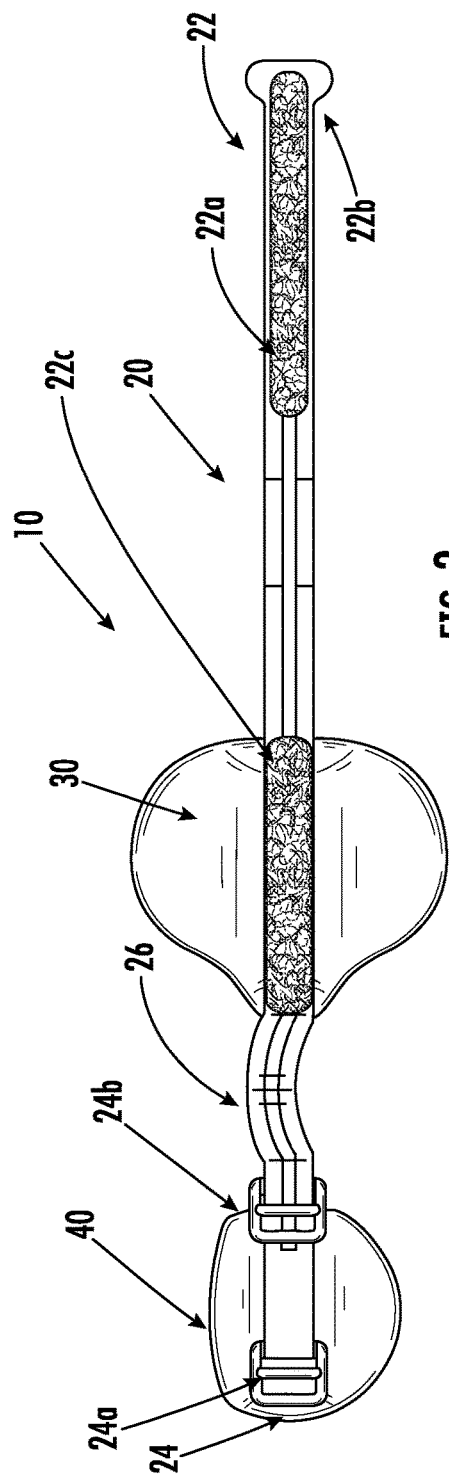
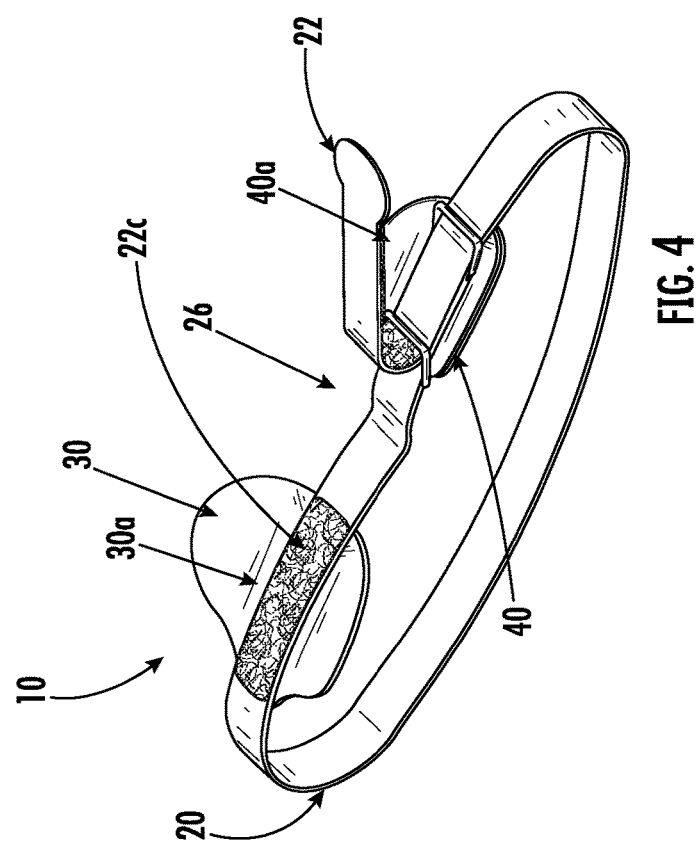
FIG. 3
FIG. 4

WRIST BRACE STRAP

RELATED APPLICATIONS

This application claims priority to U.S. Provisional Application Ser. No. 63/055,576, filed Jul. 23, 2020, the disclosure of which is incorporated by reference in its entirety.

FIELD OF THE INVENTION

The invention relates generally to devices for supporting the wrist.

BACKGROUND OF THE INVENTION

The wrist consists of eight bones appearing in two rows. The proximal row of carpal bones consists of the scaphoid, lunate, triquetrum, and pisiform and articulates with the distal ends of the radius and ulna as well as the distal row of carpal bones (except the pisiform). The distal row of carpal bones consists of the trapezium, trapezoid, hamate, and capitate and articulates with the proximal row of carpal bones and the proximal ends of the metacarpal bones.

The structure of the carpal bones and corresponding ligaments allows motion in the plane of flexion and extension (up and down) and radial and ulnar deviation (side-to-side) as well as motions in between these planes. Stability of this highly mobile area relies on a synchronized system of muscles, tendons, and ligaments. This area is prone to injury at least in part because of its anatomical complexity. For instance, there are multiple carpal instability patterns in which one or more carpal bones move excessively in relation to the surrounding bones, including scapholunate dissociation, perilunate dislocation, midcarpal dislocation, and lunate dislocation. These serious injuries often require surgical stabilization. In addition, functional loading of the wrist is challenging when hypermobility is present because the individual lacks the needed stability at the wrist to be able to transmit power through the tendons to the hand-individuals with hypermobility, especially those with a condition called Ehlers Danlos Syndrome, move excessively at their joints and their tendons may bowstring away from the underlying bones.

Existing wrist support devices for injury prevention and recovery do not provide adequate support while permitting a sufficient range of motion of the wrist. For example, individuals with hypermobility or who have adaptively elongated wrist ligaments from repeated weight bearing (such as from gymnastic exercises, manual labor, etc.) would benefit from a wrist support during such tasks, but often the available wrist supports do not provide a sufficient range of motion to adequately perform those tasks. As such, an improved wrist brace may be desired which provides support to the wrist joint while permitting an improved or larger range of motion.

SUMMARY

According to some embodiments of the invention, A wrist brace for providing support to carpal bones within a wrist of the user, the wrist brace comprising an elongated strap sized and configured to encircle a wrist; a first bracing member on the strap and configured for positioning on a volar side of a wrist; and a second bracing member spaced apart from the first bracing member on the strap and configured for positioning on the dorsal side of a wrist; wherein the first and second bracing members extend outward from the elongated strap and have a surface area that, together with the elongated strap, supports the carpal bones within the wrist.

In some embodiments, the second bracing member comprises a compliant or rigid material or a pre-formed hyperbolic paraboloid.

In some embodiments, the first bracing member comprises a compliant curved or flat sheet.

In some embodiments, a thickness of the first bracing member is uniform across its surface area or is greater in a central portion thereof as compared to a peripheral portion thereof.

In some embodiments, at least one of the first and second bracing members are slidably attached to the strap so as to move with respect to the other of the first and second bracing members.

In some embodiments, a thickness of the second bracing member is greater in a central portion thereof as compared to a peripheral portion thereof.

In some embodiments, the first and second bracing members are formed of a polymeric material.

In some embodiments, the elongated strap in the use position is approximately distal to the radius and ulna and approximately proximal to the metacarpals.

In some embodiments, an axial width of the elongated strap is between 0.5 cm and 3 cm.

In some embodiments, the elongated strap is formed of a material that has an increased tensile stiffness along its length as compared to its width.

In some embodiments, the second bracing member has a length along the elongated strap of about 3 to 7 cm and a width of about 3 to 10 cm.

In some embodiments, the first bracing member has a length along the elongated strap of about 2 to 5 cm and a width of about 3 to 7 cm.

In some embodiments, the first bracing member is positioned on the elongated strap such that, in use, the first bracing member is located over at least one selected carpal bone for stabilization.

In some embodiments, the first bracing member comprises a top portion above the strap that forms a curved extension that faces a palm of a hand of the user and an extended lower portion that extends away from the hand along an arm of the user and has a curved, rectangular shape and located, in use, over at least one selected carpal bone for stabilization.

In some embodiments, the elongated strap comprises a closing unit configured to adjustably close and constrain the elongated strap in use on or around a wrist.

In some embodiments, the first and second bracing members are configured to distribute pressure on surfaces thereof.

According to some embodiments, a method for supporting the carpal bones of a wrist includes positioning a wrist brace circumferentially over and around the carpal bones of the wrist, wherein the wrist brace comprises: an elongated strap sized and configured to encircle a wrist; a first bracing member on the strap and configured for positioning on a volar side of a wrist; and a second bracing member spaced apart from the first bracing member on the strap and configured for positioning on the dorsal side of a wrist; wherein the first and second bracing members extend outward from the elongated strap and have a surface area that, together with the elongated strap, supports the carpal bones within the wrist.

In some embodiments, positioning a brace over and around the carpal bones of the wrist comprise positioning a brace approximately distal to the radius and ulna and approximately proximal to the metacarpals.

BRIEF DESCRIPTION OF THE FIGURES

FIG. 3 is a top view of the wrist brace of FIG. 1.

FIG. 4 is a perspective view of the wrist brace of FIG. 1 in a closed position.

DETAILED DESCRIPTION

Figure 1:
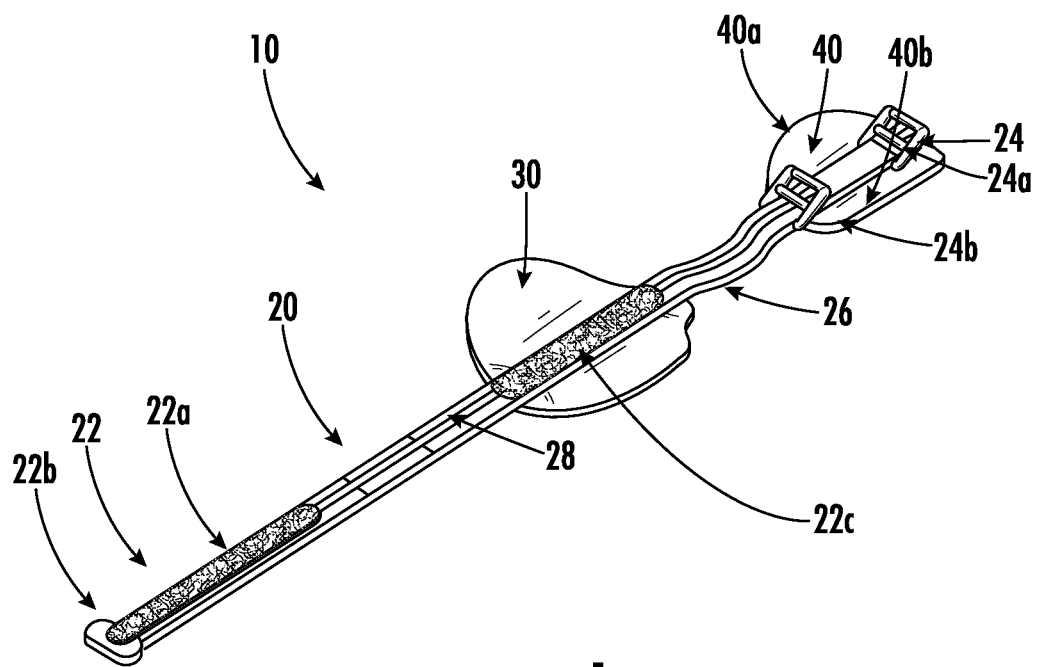
FIG. 1 is a top perspective view of a wrist brace according to some embodiments of the present invention.
Figure 2:
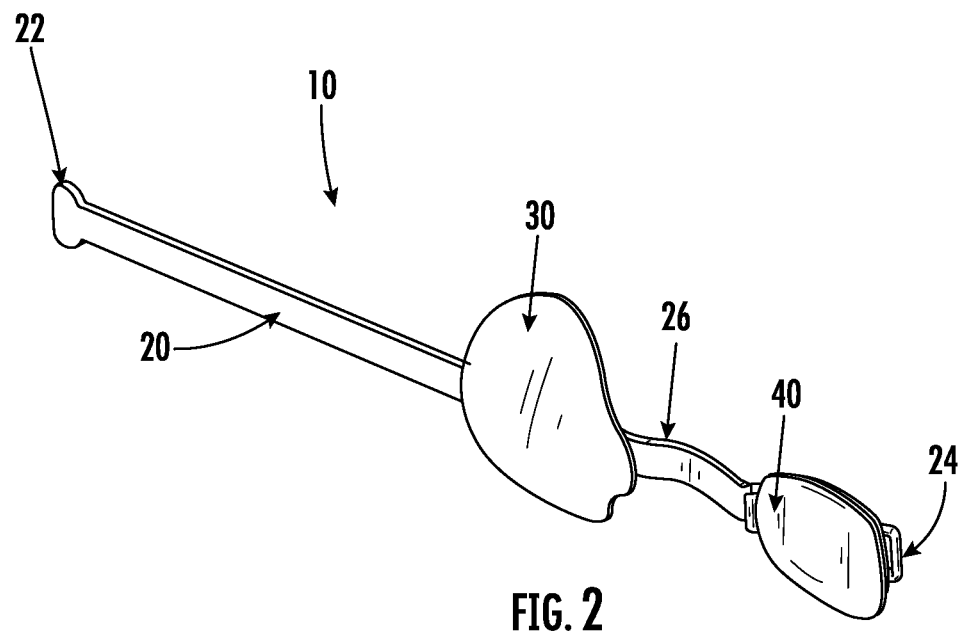
FIG. 2 is a bottom perspective view of the wrist brace of FIG. 1.
Figure 5:
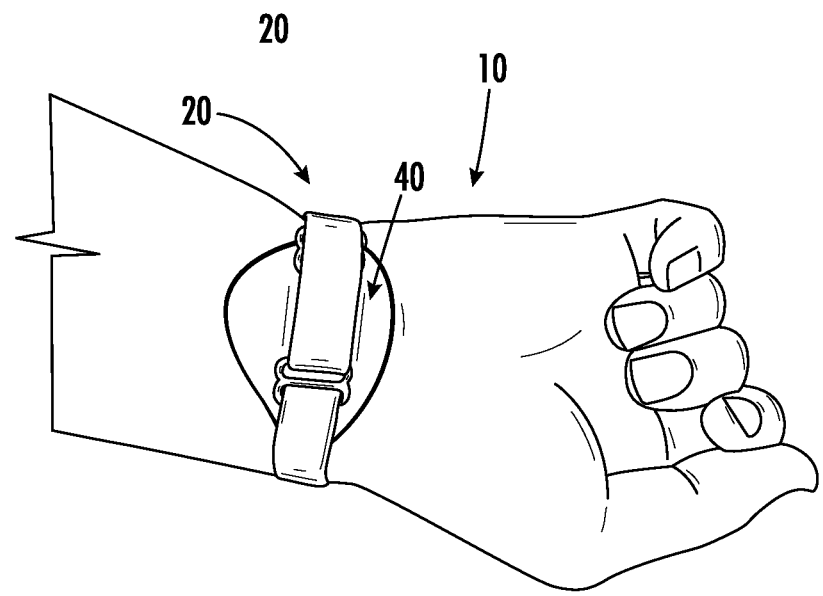
FIG. 5 is a volar side view of the wrist brace of FIG. 1.
Figure 6:
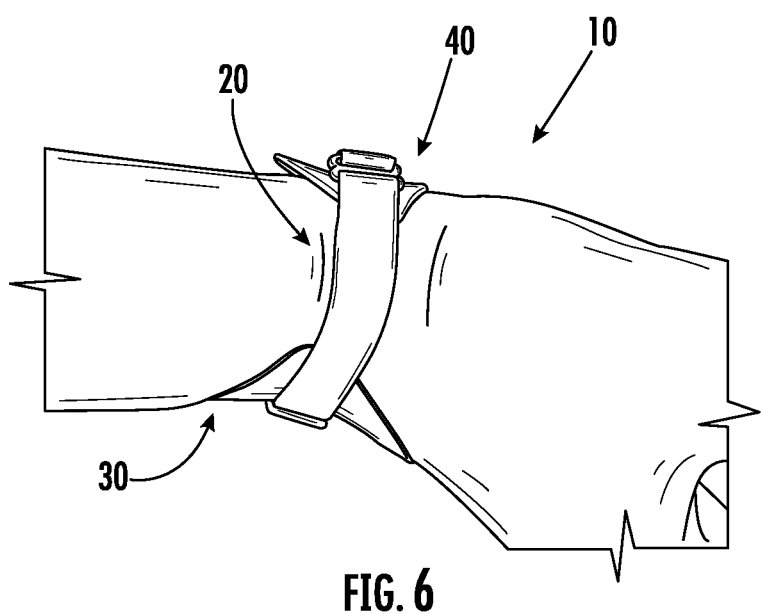
FIG. 6 is a radial side view of the wrist brace of FIG. 1.

The present invention is described with reference to the accompanying drawings, in which certain embodiments of the invention are shown. This invention may, however, be embodied in many different forms and should not be construed as limited to the embodiments that are pictured and described herein; rather, these embodiments are provided so that this disclosure will be thorough and complete and will fully convey the scope of the invention to those skilled in the art. It will also be appreciated that the embodiments disclosed herein can be combined in any way and/or combination to provide many additional embodiments.

Unless otherwise defined, all technical and scientific terms that are used in this disclosure have the same meaning as commonly understood by one of ordinary skill in the art to which this invention belongs. The terminology used in the below description is for the purpose of describing particular embodiments only and is not intended to be limiting of the invention. As used in this disclosure, the singular forms "a", "an", and "the" are intended to include the plural forms as well, unless the context clearly indicates otherwise. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Referring now to the figures, FIGS. 1-8 illustrate a wrist brace 10 for providing support to carpal bones within the wrist. The wrist brace 10 includes an elongated strap 20 that is sized and configured to encircle a wrist as shown in FIGS. 5-8. The brace 10 has a bracing member 30 on the strap 20 that is configured for positioning on a dorsal side of a wrist (see FIG. 7), and a bracing member 40 spaced apart from the other bracing member 30 on the strap 20 and configured for positioning on the volar side of a wrist (see FIG. 5). The bracing members 30, 40 extend outward from the elongated strap 20 and distribute pressure along an area thereof. The bracing members 30, 40 have curved surfaces that face the wrist and, together with the elongated strap 20, support the carpal bones within the wrist.

As illustrated, the strap 20 includes two opposing ends 22, 24, a curved or angled portion 26 between the brace members 30, 40, and an optional reinforcing component 28 that may reduce strap breakage while maintaining flexibility of the ends 22, 24. The end 22 includes a hook closure component 22a with a tab end 22b, and the end 24 has one or two rings: 24a and 24b with a loop closure 22c in between. As shown in FIG. 1, the ends 22, 24 form a closure with the hook closure component 22a and tab end 22b passing through the rings 24a and 24b and adjustably held in position on the wrist by the rings 24a and 24b. The rings 24a and 24b may be a standard or double D-ring or tri-glide slides. The ends 22, 24, hook closure component 22a, tab end 22b, loop closure 22c, and rings 24a and 24b together comprise an adjustable closing unit as shown in FIG. 4; however, any suitable closure may be used, such as a hook and loop closure, buttonhole and stud, dress/skirt/garment hook and eye, tri-glide slides, cam buckle, ratchet buckle, release plastic buckle, dual adjustable buckle, tongue buckle, or other type of buckle or releasable closure, such as a releasable zip tie closure. Moreover, in some embodiments, the curved or angled portion 26 may be configured as a straight or linear portion that forms a substantially continuous circular shape of the strap 20 in position on a user's wrist. For example, a strap material that is compliant to the bony shapes of the wrist (but does not stretch around the circumference) may be used.

As shown, e.g., in FIG. 4, the bracing member 30 has a curved surface 30a that forms a hyperbolic paraboloid shape. The surface 40a of the bracing member 40 is generally flatter and compliant. The bracing members 30, 40 distribute pressure from the strap 20 and further stabilize or brace the wrist. As illustrated in FIG. 4, the underside of the bracing member 30 that is curved outwards in the longitudinal plane, faces toward and touches the wrist when the strap 20 is closed, and the underside of the bracing member 30 that is curved inwards in the transverse plane also faces towards and touches the wrist. In this configuration, the bracing members 30, 40 restrict motion by providing increased support, and consequently, decreased motion, adjacent the strap 20 and decreased support along the edges of the bracing members 30, 40 away from the strap 20. In some embodiments, both the bracing members 30, 40 may have a curved and/or hyperbolic shape. In some embodiments, the bracing member 40 has a curved edge side 40a and a truncated or flat edge side 40b. The reduced width on the edge side 40b may permit increased range of motion and comfort to the wearer while reducing injury or strain on the wrist.

In some embodiments, the bracing members 30, 40 may further have a variable thickness such that a center portion of the bracing members 30, 40 are thicker than the edge portion. For example, a thickness in the center portion may be from 3.0 mm to 5.0 mm and a thickness in the edge portion may be from 1.0 mm to 3.0 mm. In this configuration, the edge area of the bracing members 30, 40 may have a greater flexibility than the center portion such that increased stabilization to the wrist is provided in the center of the bracing members 30, 40 corresponding to the volar and dorsal portions of the wrist, respectively, while allowing movement of the wrist. The bracing members 30, 40 may be formed of a polymeric material. In some embodiments, the bracing members 30, 40 are formed of a polymeric material, such as urethane sheeting material with a Shore of about A90. The total thickness may range from 1.0 mm to 5 mm, or in particular embodiments, from 3.0 mm to 4 mm. When the interior region is thicker, the area or shape of the thicker region may differ. The thicker interior region may be an oval that is parallel to the long axis of the arm or across the long axis of the arm. Circular or rectangular regions may also be used, or the thickness may be gradually changed from the interior to the exterior of the brace member.

Figure 7:
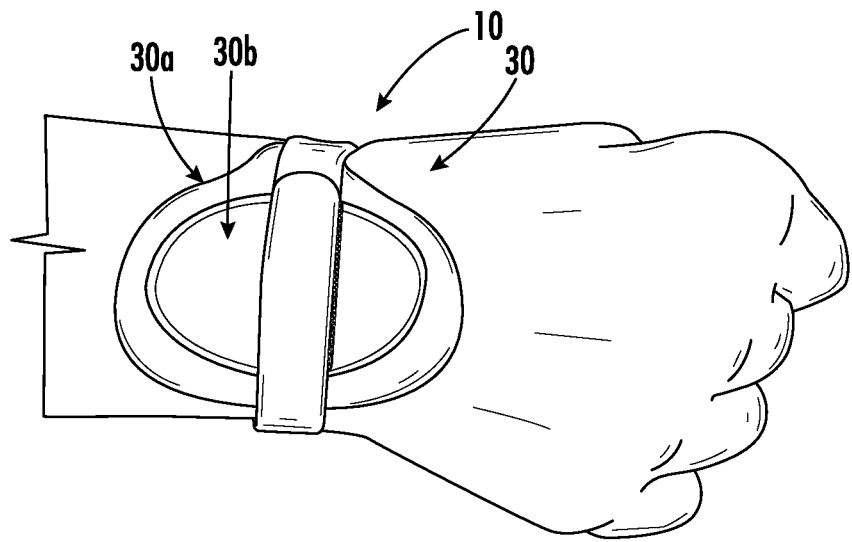
FIG. 7 is a dorsal view of the wrist brace of FIG. 1.
Figure 8:
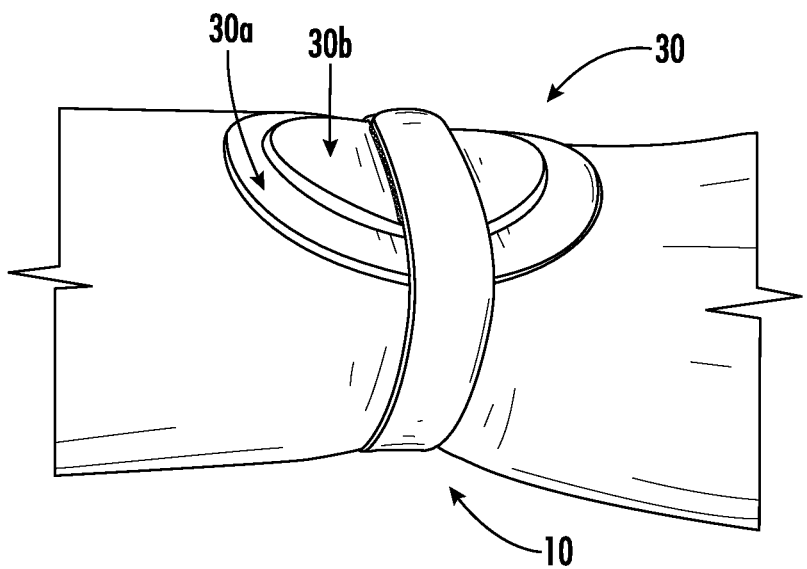
FIG. 8 is an ulnar view of the wrist brace of FIG. 1.

Accordingly, the bracing members 30, 40 are configured to distribute pressure on surfaces thereof to decrease undue restriction or pressure points along the wrist. Thus, the tensile stiffness of the brace members 30, 40 may vary from an edge region to the center region, with the edge region being generally more flexible than the center portion. In some embodiments, the center region is thicker than the edge region. As illustrated in FIGS. 7-8 the brace member 30 may have a bottom layer 30a and a top layer 30b such that the top layer 30b provides additional thickness, and consequently, tensile stiffness, to the center region of the brace member 30. This dual layer configuration may also be used in the brace member 40. However, any suitable thickness and tensile stiffness, including variable thickness and/or tensile stiffness may be used. In some embodiments, the thickness and tensile stiffness may be uniform across the area of the brace members 30, 40. In some embodiments, the brace members 30, 40 may be formed of a single unitary member rather than being formed of separate layers, and the thickness can vary from the center to the edge portion in a gradual manner. The brace members 30, 40 may be formed by any suitable method, including injection molding and additive manufacturing. The brace members 30, 40 may be formed of a polymeric material, which may optionally be filled and/or fiber reinforced.

In some embodiments, the strap 20 is positioned on the carpal bone area of the wrist. In particular, the carpal bones are eight small bones in the wrist with the trapezium, trapezoid, capitate, and hamate bones generally on a distal row adjacent the metacarpal bones and the scaphoid, lunate, triquetrum, and pisiform bones on a proximal row distal to the radius and ulna bones of the arm. The strap 20 as shown in FIGS. 5-8 may be positioned approximately between the top and bottom rows of the carpal bones, i.e., so that the strap 20 in a use position is over and around the carpal bones.

The reinforcing component 28 is formed of a material that is stiffer than the main portion of the strap 20 and lies in the center of strap 20 along its full length extending to the hook component 22a to provide additional bracing support. As shown, the reinforcing component 28 does not extend fully underneath the hook component 22a, such that the hook component 22a remains flexible for ease of use in closing the brace 10 around the wrist. It should be understood that in some embodiments, the reinforcing component 28 may be omitted.

The curved or angled portion 26 of the strap is configured to lie, in use, distal to the distal end of the radial styloid and in some embodiments may have two small silicone pads on the inner surface of the strap intended to be placed on each side the abductor pollicis longus tendon which is prominent distal to the radial styloid. Although the curved portion 26 is illustrated with a curvilinear shape, any suitable angled portion may be used, including two straight lines with an angle at the current curve location. In some embodiments, the portion 26 may be a straight line with the curve omitted.

In some embodiments, the axial width of the elongated strap 20 is less than about 30 mm.

The second bracing member 30 has a length along the elongated strap 20 of about 3 to 7 cm and a width of about 3 to 10 cm. The first bracing member 40 has a length along the elongated strap 20 of about 2 to 5 cm and a width of about 3 to 7 cm.

In some embodiments, the wrist brace 10 provides targeted support to the carpal bones. For instance, the strap 20 may only overlie the portion of the wrist containing the carpal bones and not substantially overlap any portion of the metacarpal bones, the radius, or the ulna. Specifically, the strap 20 may lie within an area of the wrist bounded between the most proximal surface of a carpal bone within the proximal row of carpal bones and the most distal surface of a carpal bone within the distal row of carpal bones. In some embodiments, the strap 20 may be situated substantially over the carpal bones while only slightly overlapping at least one of the metacarpals, the radius, and/or the ulna. In particular, although all of the strap 20 (or a majority proportion thereof) may overlie the carpal bones, a flexible portion of the wrist brace 10 (either the strap 20 or the bracing members 30, 40) may extend beyond such a region.

Advantageously, the wrist brace 10 of the present invention may provide direct support to the wearer's wrist without substantially affecting the wrist's range of motion. When the wrist is in a neutral position (i.e., zero degrees), its circumference is generally less than when it is in either flexion or extension. It is believed that the movement of the carpal bones and corresponding tendons may contribute to the circumferential expansion of the wrist during articulation. In some embodiments, the wrist brace 10 encircles the wrist with sufficient tensile stiffness to constrain or impede the wrist's natural circumferential expansion during articulation, stabilizing the carpal bones and protecting the corresponding ligaments. The constraining effect of the wrist brace 10 around the wearer's wrist may also advantageously move and/or stabilize the arrangement of tendons passing through the wrist, thereby stabilizing the moment arms of the tendons, minimizing bowstringing of the tendons away from underlying bones, and reducing friction on the tendons, among other examples. In addition, localized compression of the carpal bones may aid in improved proprioception of the wrist joint. Targeted compression to the distal radioulnar joint may also reduce wrist pain resulting from injuries to the triangular fibrocartilage complex and/or the distal radioulnar joint itself. The brace 10 may be used in a rehabilitative and/or preventative fashion to manage or prevent symptoms from repetitive tasks such as repetitive use of tools or machinery, bowling, playing tennis, golfing, working on an assembly line, gardening, cleaning, and the like.

While providing any one or more of the above-noted advantages, the wrist brace 10 may only restrict the range of motion of the wearer's wrist minimally, if at all. For instance, the range of motion of the wearer's wrist may only decrease by less than about 20 degrees in any direction as a result of wearing the brace. In some embodiments, the restriction on the range of motion may be about 0 degrees.

In some embodiments, however, the wearer may desire to intentionally restrict the wrist's range of motion, even to restrict the range of motion by a particular amount or in a particular direction, and the wrist brace 10 may be configured to restrict the range of motion by greater than about 10 degrees. In some embodiments, a stiffer second bracing member may be used to intentionally provide greater restriction to wrist motion in any direction.

The strap 20 may be any suitable width or length. In some embodiments, the strap 20 has a width of greater than about 5 mm, up to as much as 30 mm. Although the strap 20 is illustrated as formed of a different material than the bracing members 30, 40, in some embodiments, at least a portion of the strap 20 may be formed of the same material. In some embodiments, the bracing members 30, 40 are formed of a single unitary member and connected by at least a portion of the strap 20.

The material (or material mixture) of the strap 20 is sufficiently compliant so as to flexibly bend around the wrist of the user. In some embodiments, the strap 20 is compliant along its width, but has an increased tensile stiffness along its length as compared to its width. With a compliant width and increased tensile strength along its length, the strap 20 forms a substantially fixed circumference around the wrist to provide additional stability for the wrist. That is, the strap 20 may form a loop around the user's wrist that is of substantially uniform circumference, when in position, and generally does not stretch along its length, which stabilizes the wrist. However, in some embodiments, the strap 20 may be compliant along its width to permit flexing of the wrist and increased comfort to the user. The strap 20 may be formed of any suitable material, such as woven or non-woven materials, nylon, an in-elastic material, leather, thermoplastic elastomers (e.g., styregnic block copolymers, polyolefinelastomers, vulcanizates, polyurethanes, copolyesters, polyamides, and the like) and rubber materials (e.g., neoprene, nitrile, butyl, and vinyl rubbers, and the like). Some embodiments include silicone polymers or copolymers.

In some embodiments, the brace 20 applies a radially compressive force to the wrist while bracing the wrist via the bracing members 30, 40. In some embodiments, methods of the present disclosure comprise the step of supporting the wrist with the brace while permitting some range of motion for daily activities or athletic activities. In some embodiments, the brace applies a radially compressive force effective to at least partially stabilize the wrist. In some embodiments, the brace impedes the circumferential expansion of the wrist area as the wrist articulates.

Although the brace members are illustrated as separate members, the volar and dorsal brace member may be formed as an integral unit that is connected by a strip (not shown) or integrated with the strap.

Figure 9:
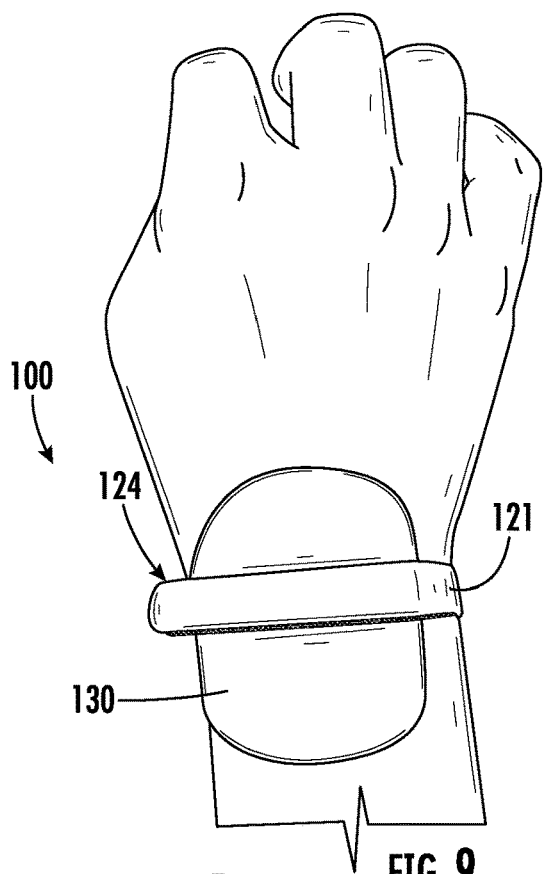
FIG. 9 is a dorsal view of a wrist brace in position on a wrist according to some embodiments of the present invention.
Figure 10:
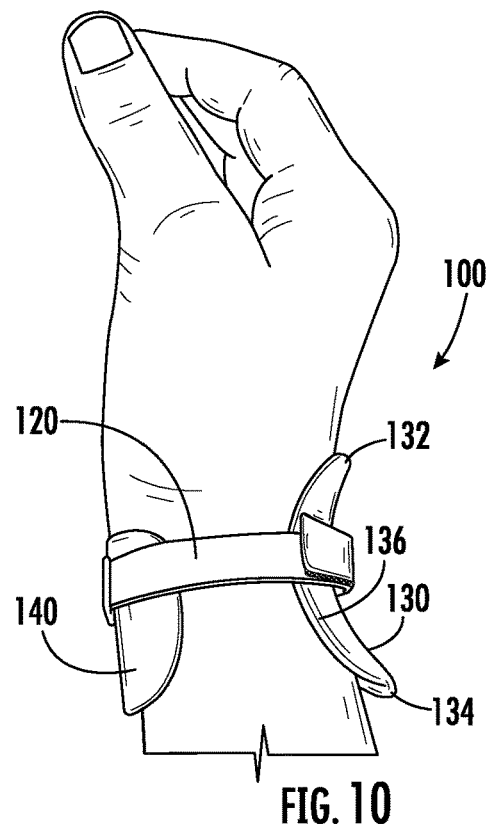
FIG. 10 is a radial view of the wrist brace of FIG. 9.
Figure 11:
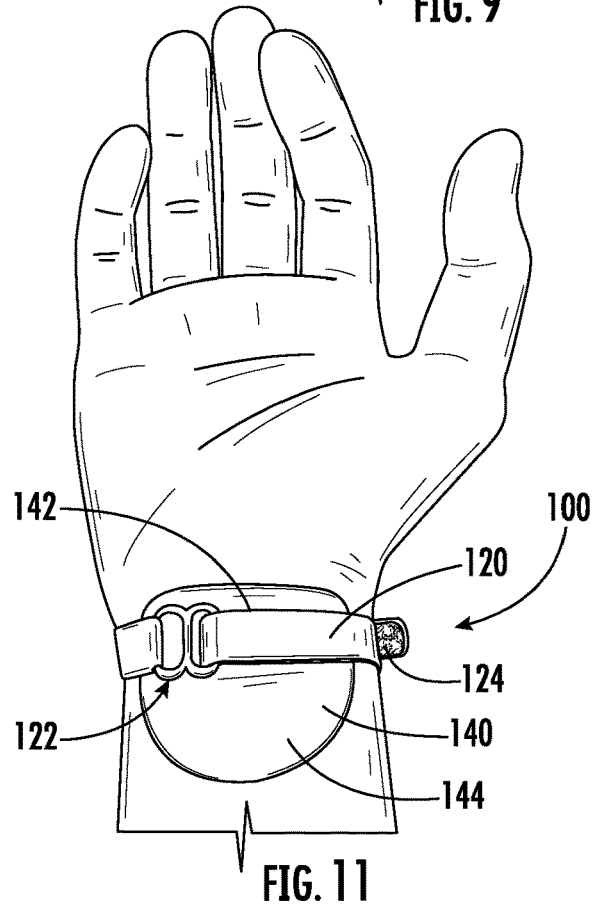
FIG. 11. is a volar view of the wrist brace of FIG. 9.
Figure 12:
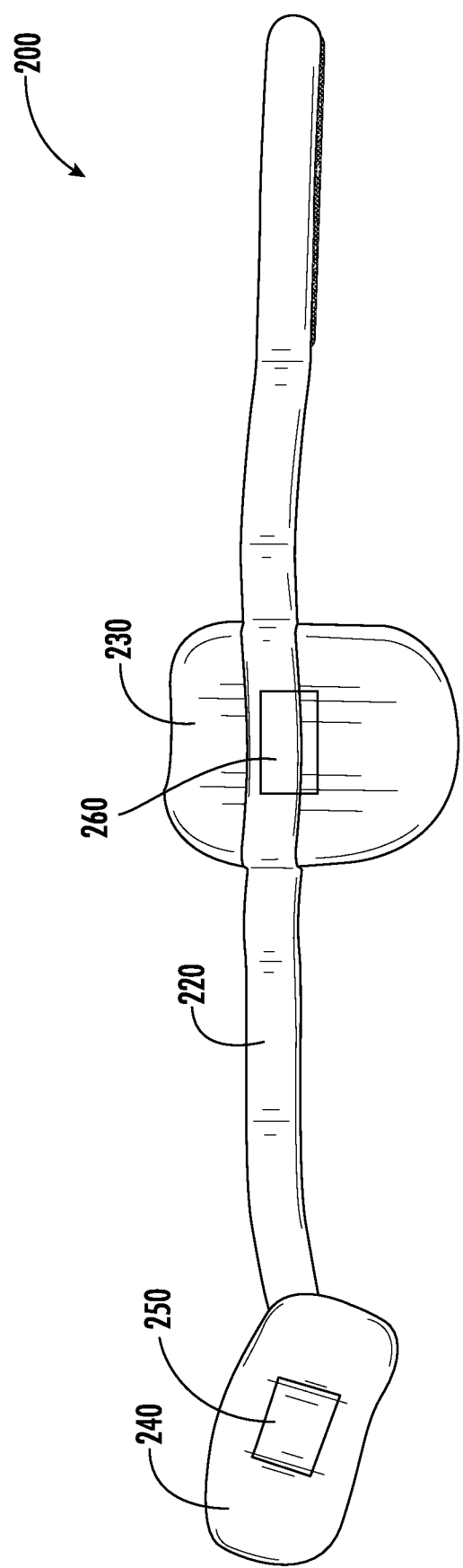
FIG. 12 is a bottom planar view of a wrist brace according to some embodiments of the present invention.
Figure 13:
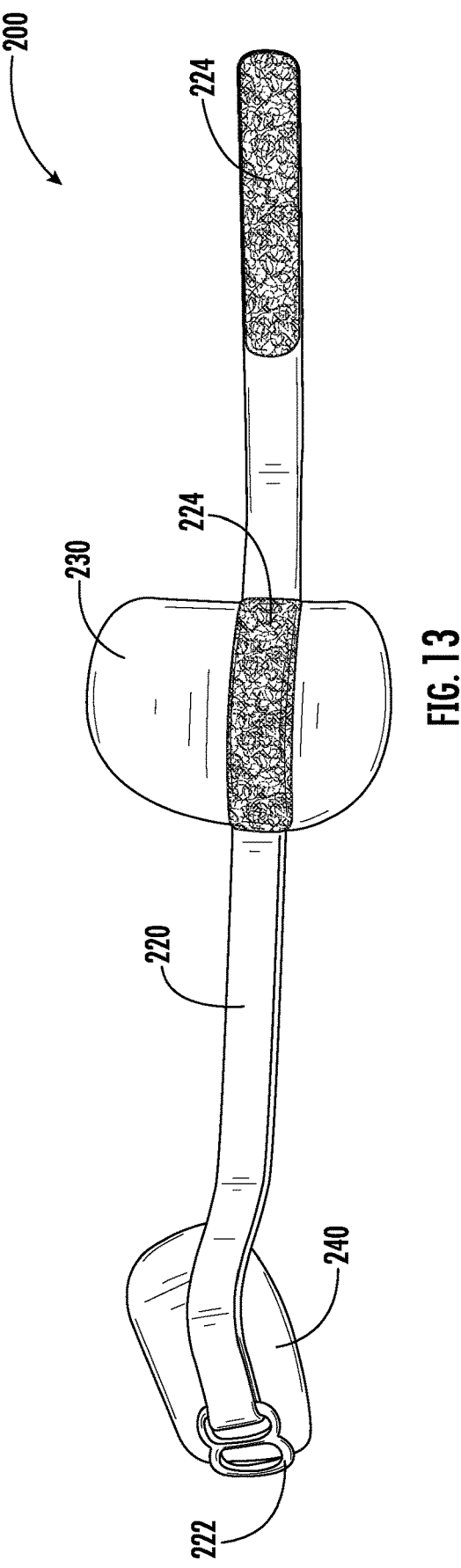
FIG. 13 is a top planar view of the wrist brace of FIG. 12

Although embodiments according to the present invention are described with respect to the wrist brace 10 of FIGS. 1-8, additional configurations may be used. For example, as shown in FIGS. 9-11, a wrist brace 100 includes a strap 120, a dorsal side bracing member 130 and a volar side bracing member 140. As illustrated in FIGS. 9 and 11, the strap 120 has a closure mechanism including a ring 122 and a hook and loop connection 124. The ring 122 is attached to one end of the strap 120 so that the other end of the strap 120 is passed through the ring 122 and fastened at the hook and loop connection 124 to form an adjustable circumference around the user's wrist. Once the hook and loop connection 124 is fixed, the strap 120 is held in a fixed position on the user's wrist without substantial variations in the circumference of the strap 120. In the embodiments shown in FIGS. 9-11, the bracing members 130, 140 are substantially uniform in thickness. The curved or angled portion 26 of the strap 20 shown in FIGS. 1-8 is omitted, and the strap 120, when not in position on a wrist, is linear. As shown in FIGS. 9 and 11, the bracing members 130, 140 are generally opposite one another and configured for positioning in a central portion on the radial of the wrist. As shown in FIG. 10 the dorsal bracing member 130 is curved away from the wrist in a parabolic shape at a distal end 132 and at a proximal end 134. A middle portion 136 of the dorsal bracing member 130 curves to conform to the wrist. The volar bracing member 140 generally curves to conform to the wrist. A distal portion 142 that extends above the strap 120 as shown in FIG. 11 is shorter than a proximal portion 144 of the volar bracing member 140, which extends further away from the strap 120. However, the strap 120 may be positioned in the middle of the bracing member or towards the distal or proximal portion of the bracing member in order to provide a desired brace support.

In further embodiments of the present invention, as shown in FIGS. 12-17, a wrist brace 200 includes a strap 220, a dorsal side bracing member 230, and a volar/radial side bracing member 240. The strap 220 includes a ring connector 222 and a hook and loop connection 224 analogous to that described in FIGS. 9-11. As shown in FIGS. 14-17, the dorsal side bracing member 230 is generally on the dorso-radial side of the wrist (FIG. 15); however, the volar side bracing member 240 is off-center towards the thumb of the user. In this configuration, additional support is provided by the volar side bracing member 240 to the scaphoid bone.

Figure 14:
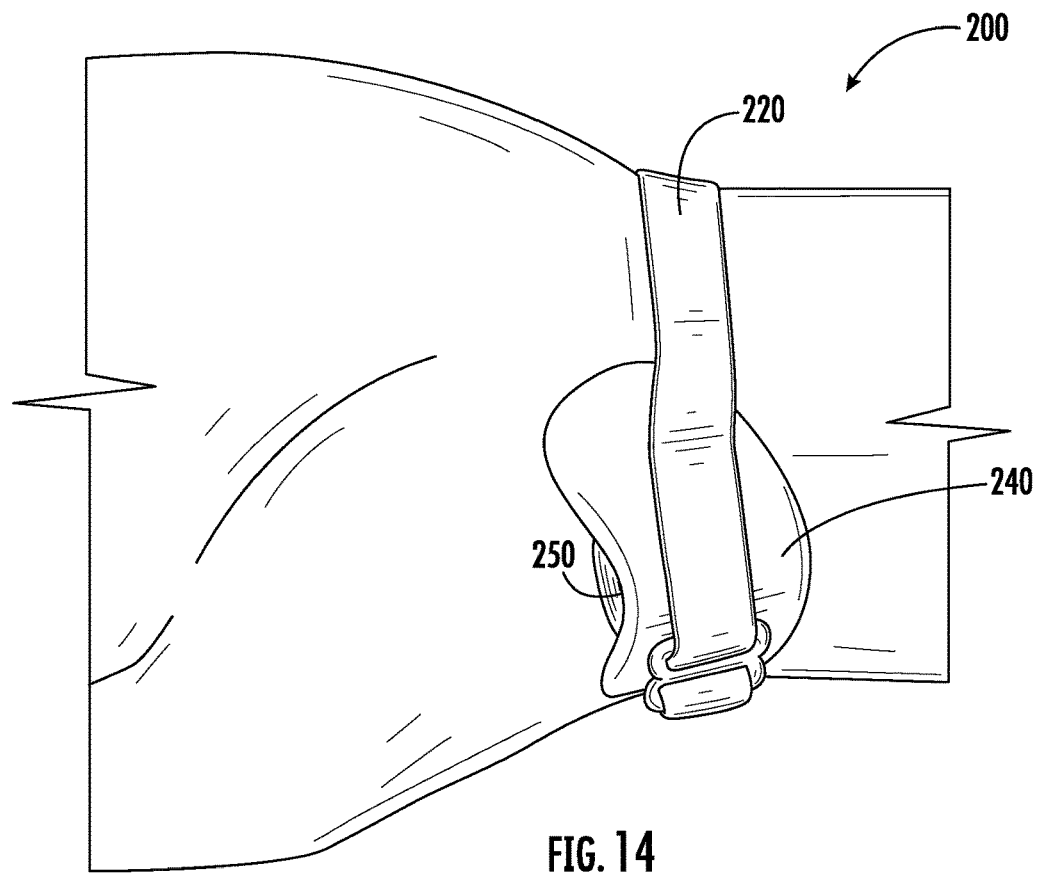
FIG. 14 is a volar side view of the wrist brace of FIG. 12 in position on a wrist.
Figure 15:
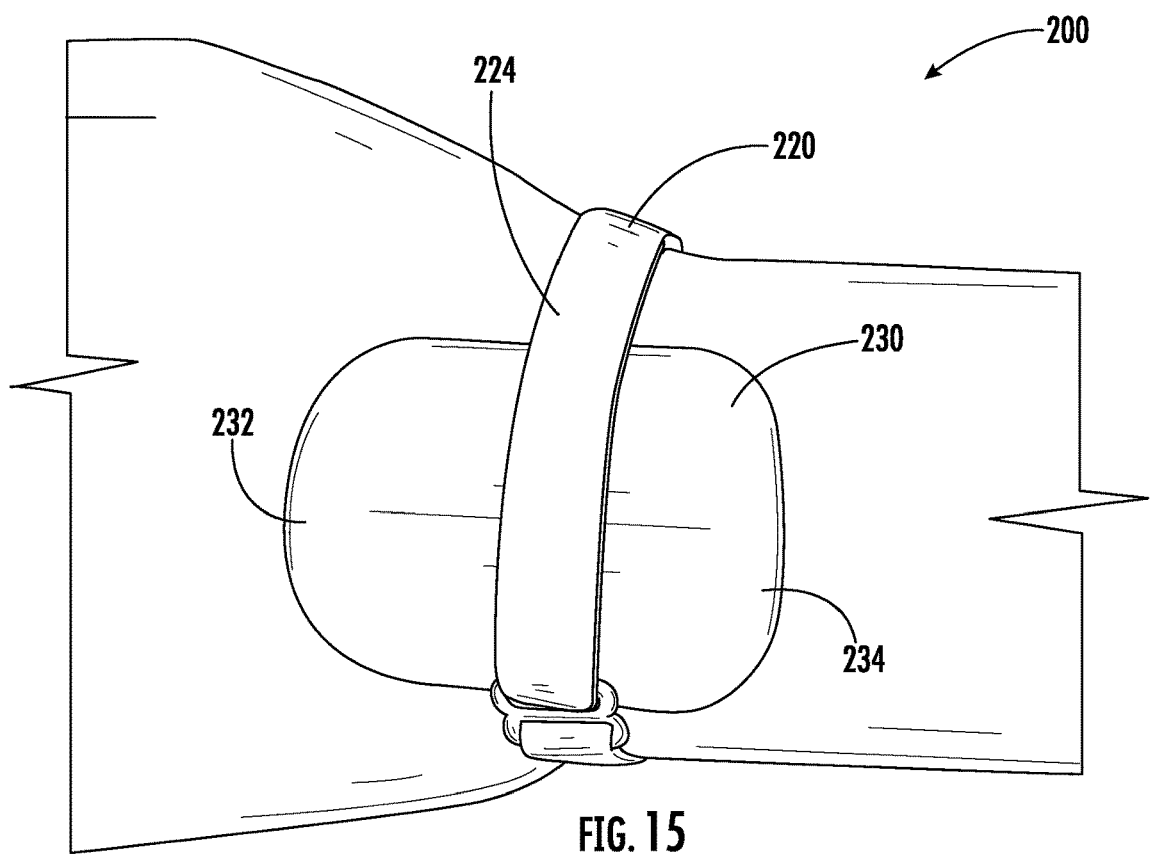
FIG. 15 is a dorsal view of the wrist brace of FIG. 12 in position on a wrist.
Figure 16:
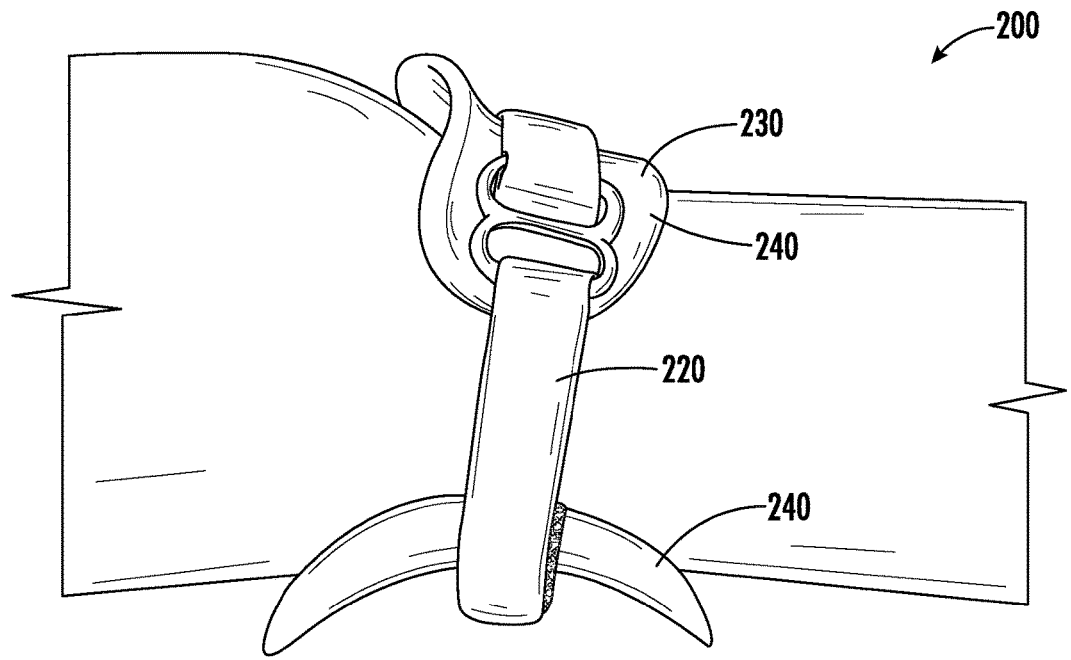
FIG. 16 is a radial view of the wrist brace of FIG. 12.
Figure 17:
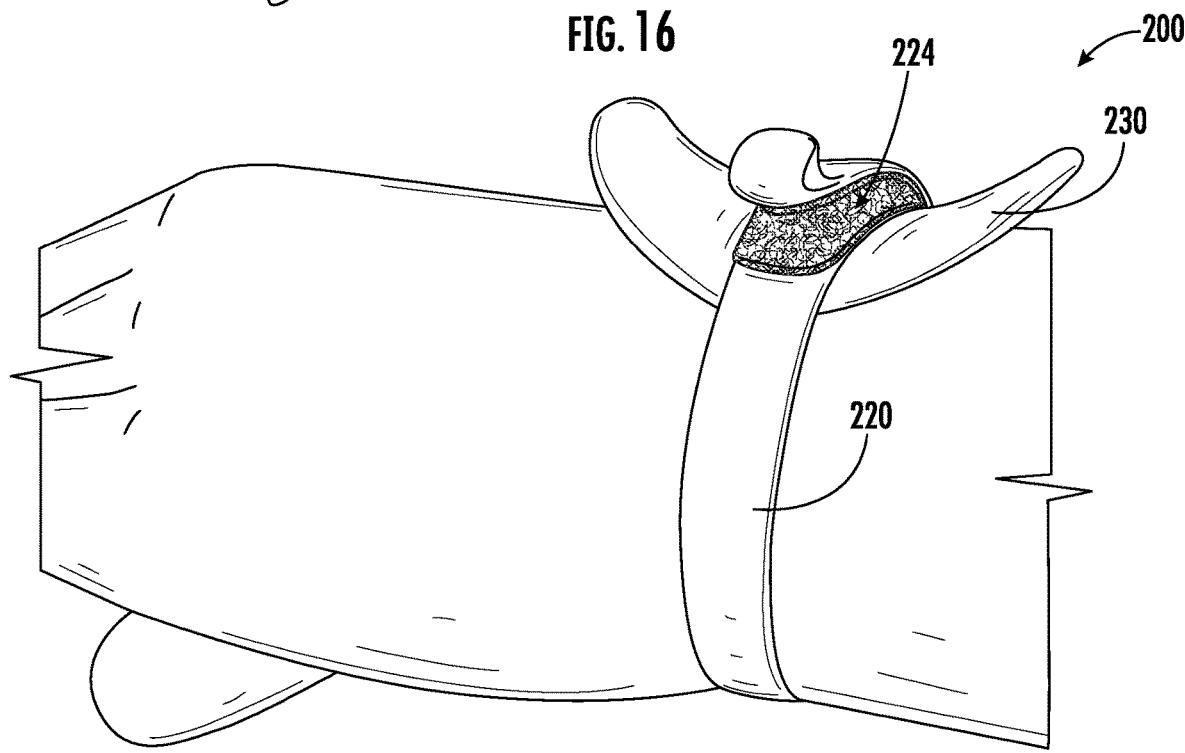
FIG. 17 is an ulnar view of the wrist brace of FIG. 12.

As shown in FIG. 14, the brace members 230, 240 may include optional pads or non-slip surface material 250. The material 250, 260 may be formed of any suitable material for cushioning and/or stabilizing the brace members 230, 240 on the skin, such as silicone, and may extend over a portion or the full user-facing surface of the brace members 230, 240.

As illustrated, the bracing members 230, 240 have a parabolic shape, and the volar bracing member 240 forms a curved shape to support the thumb side of the wrist.

Figure 18:
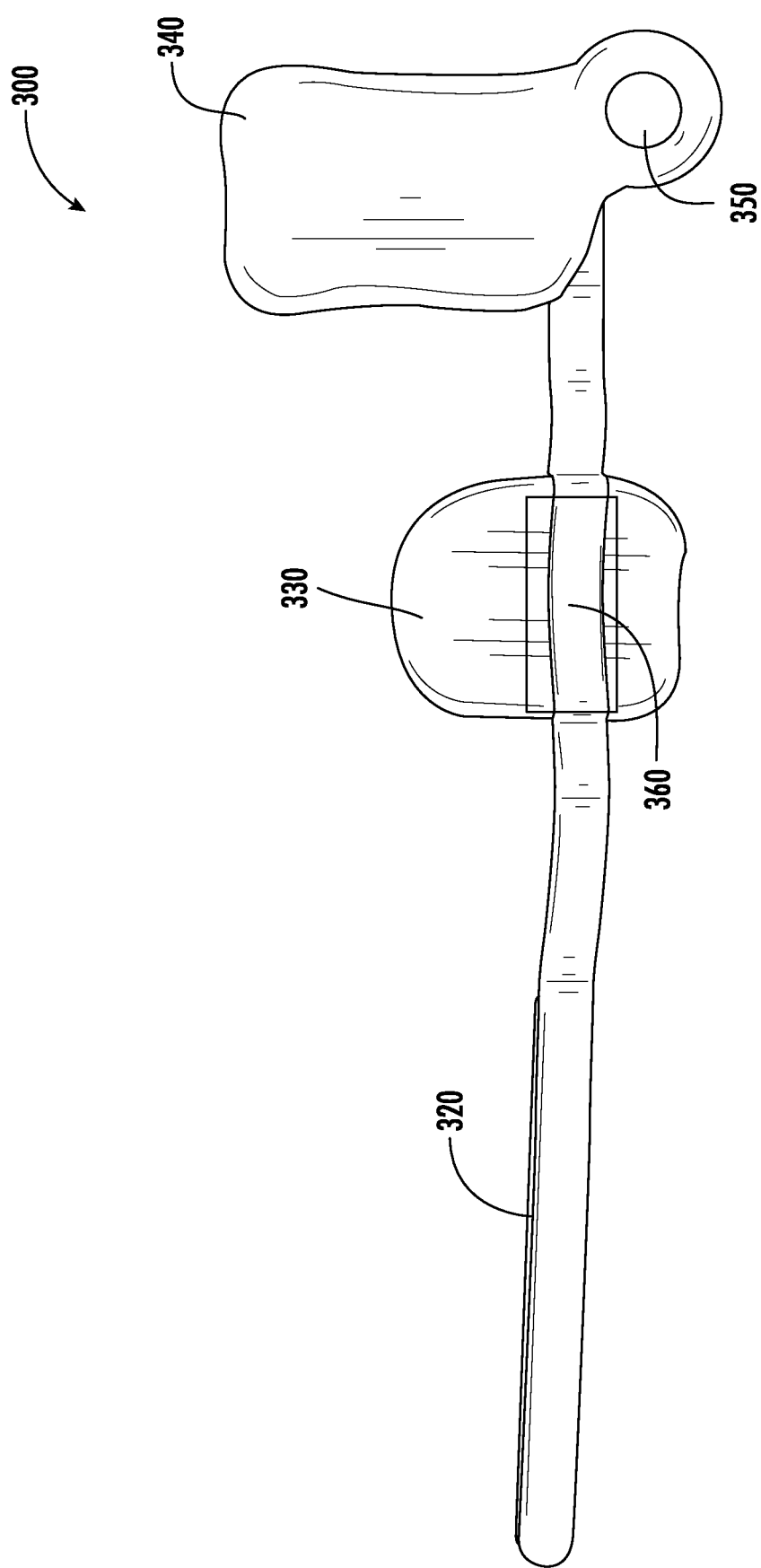
FIG. 18 is a bottom planar view of a wrist brace according to some embodiments of the present invention.
Figure 19:
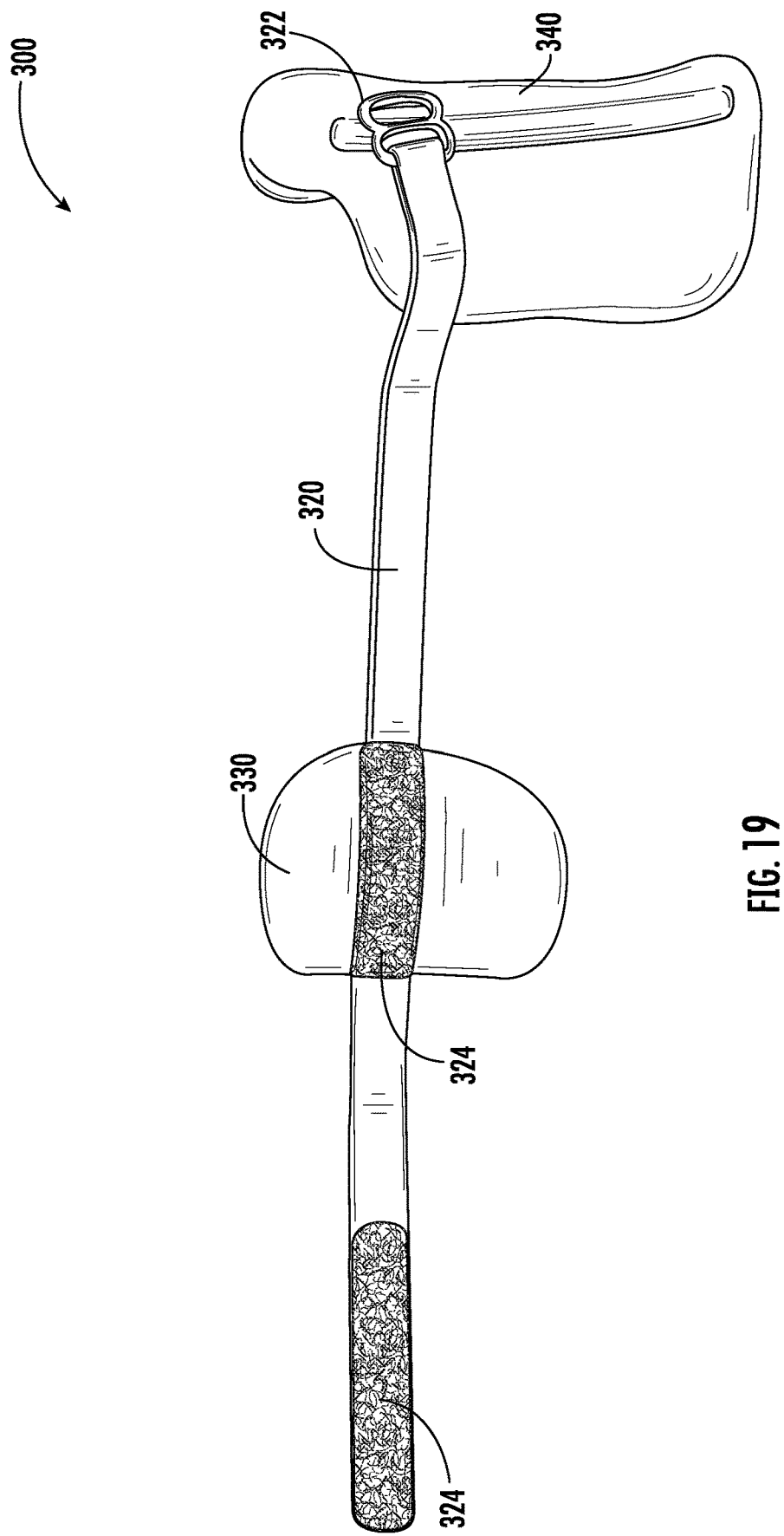
FIG. 19 is a top planar view of the wrist brace of FIG. 18
Figure 20:
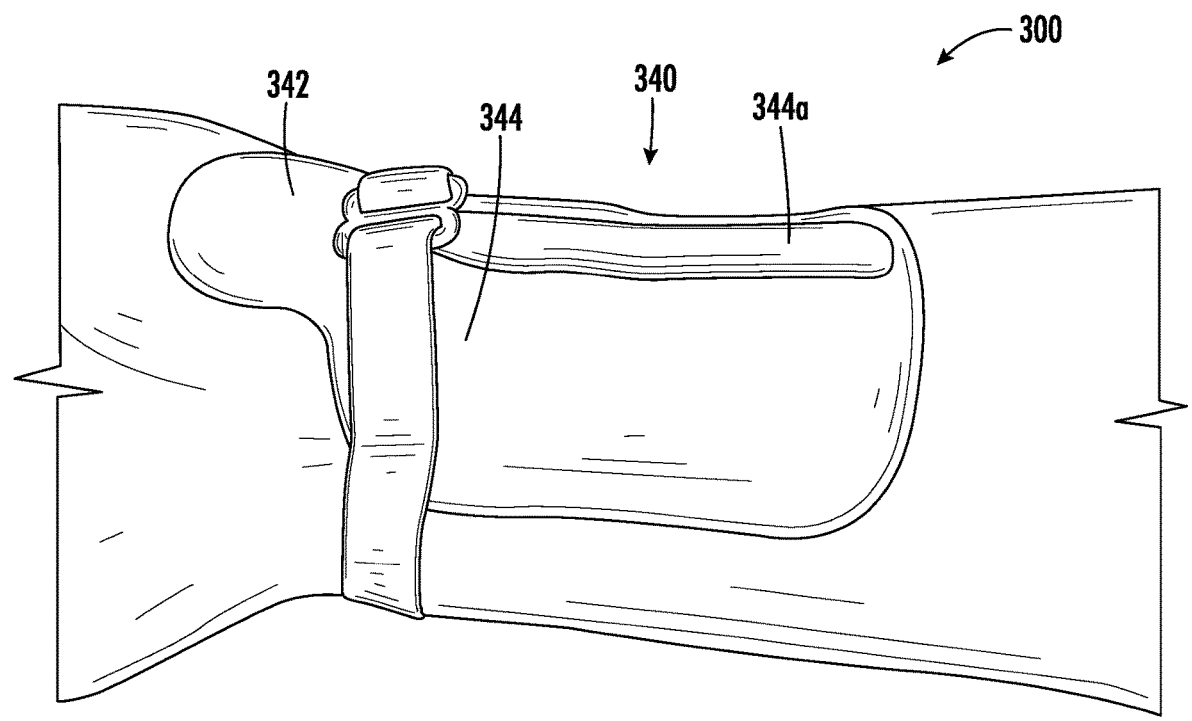
FIG. 20 is a volar side view of the wrist brace of FIG. 18 in position on a wrist.
Figure 21:
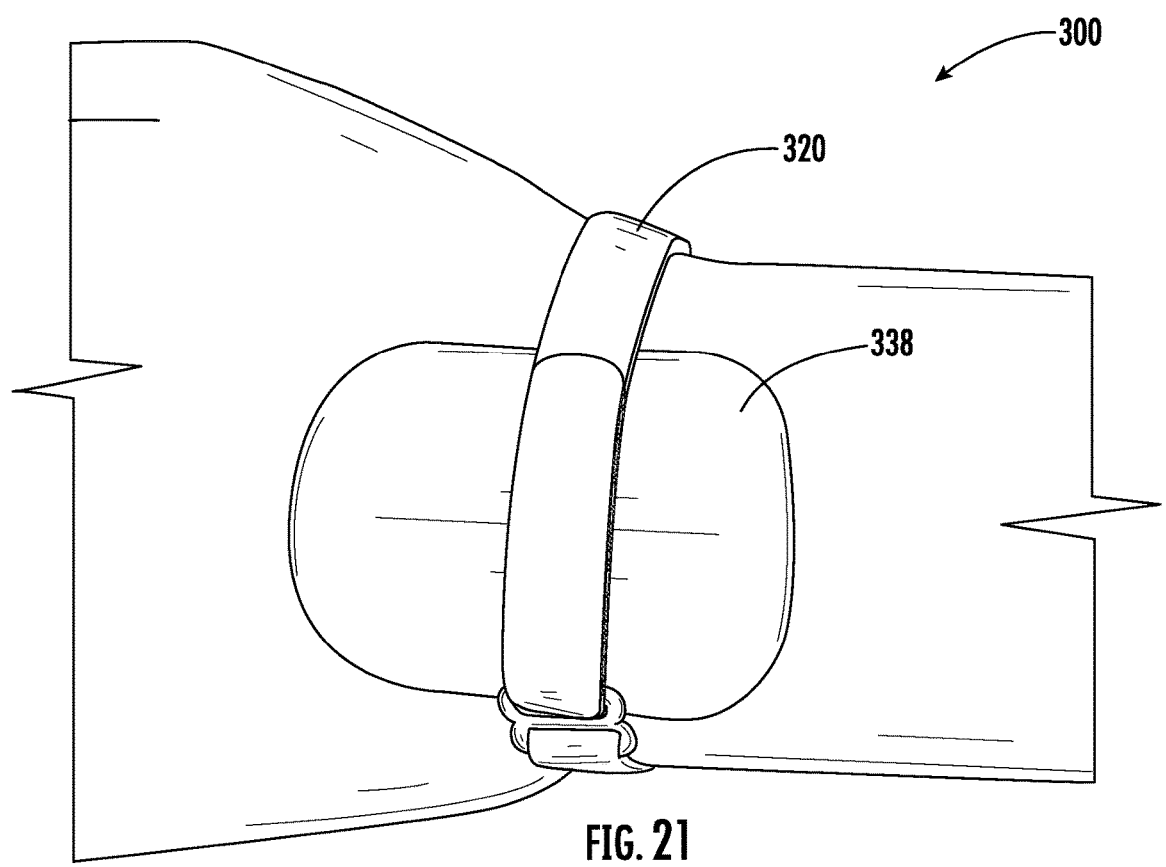
FIG. 21 is a dorsal view of the wrist brace of FIG. 18.
Figure 22:
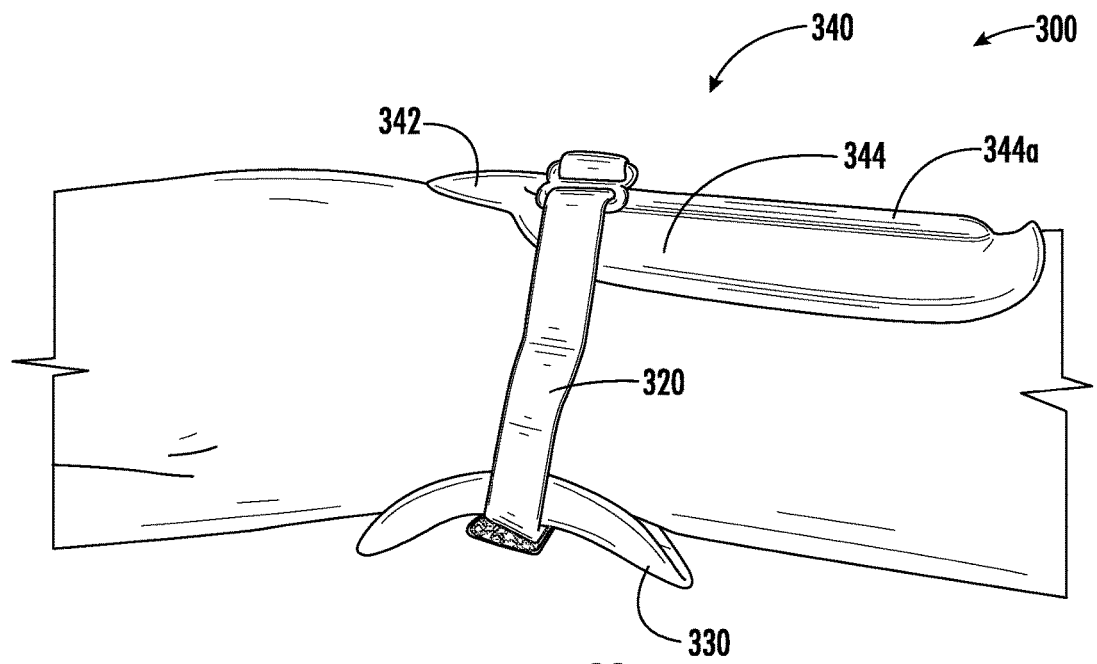
FIG. 22 is a radial view of the wrist brace of FIG. 18.
Figure 23:
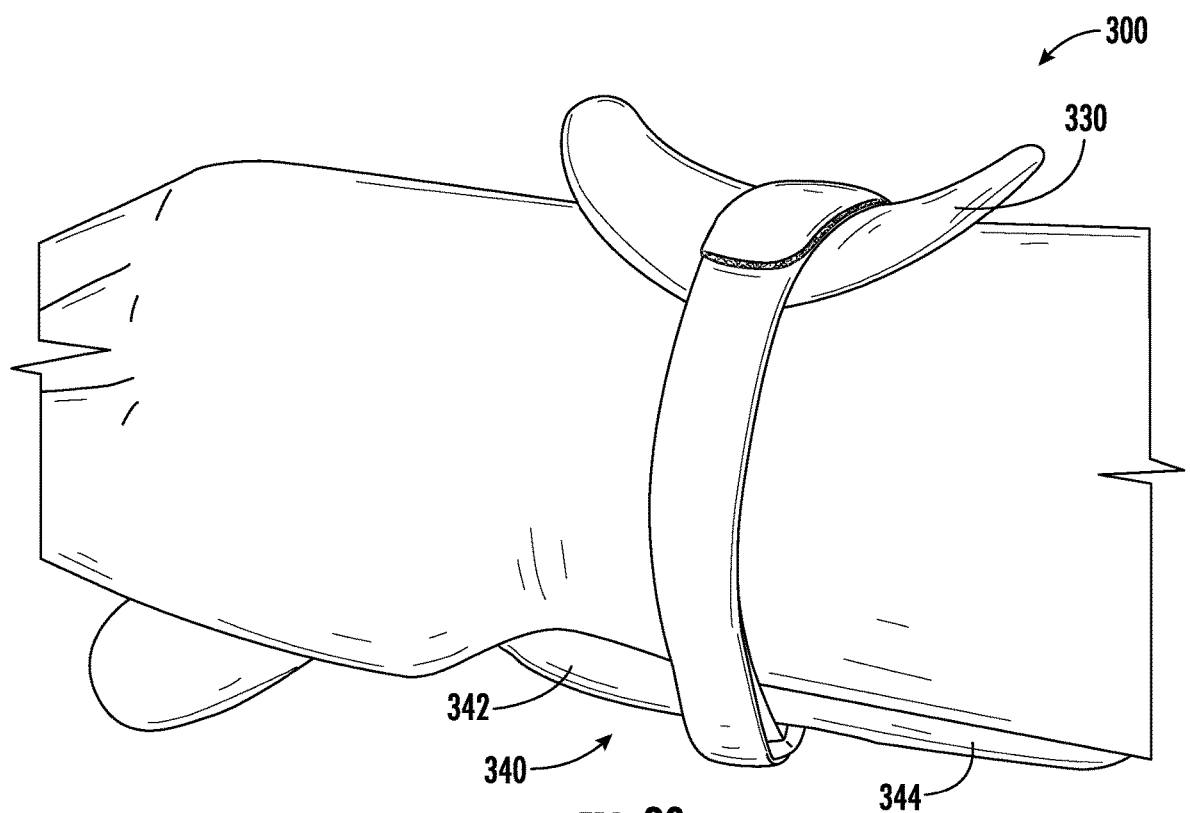
FIG. 23 is an opposing ulnar view of the wrist brace of FIG. 18.

In further embodiments of the present invention, as shown in FIGS. 18-23, a wrist brace 300 includes a strap 320, a dorsal side bracing member 330, and a volar side bracing member 340. The strap 320 includes a connector 322 and a hook and loop connection 324 analogous to that described in FIGS. 9-11. As shown in FIG. 18, the brace members 330, 340 may include optional pads or non-slip surface material 350, 360, respectively, such as silicone pads or coatings for cushioning and/or stabilizing the brace members 330, 340 against the skin. The dorsal side bracing member 330 has a size and shape that is generally similar to that described with respect to the dorsal side bracing member 230 described above. As illustrated in FIGS. 20 and 22, the volar side bracing member 340 has a curved top portion 342 that forms a perimeter having rounded or curved extension and an extended lower portion 344 that extends away from the hand and has a perimeter that has a curved, rectangular shape that is curved to generally conform to the arm. The lower portion 344 is configured to provide additional support to the wrist and arm, and the upper portion 342 provides a stabilizing force to the pisiform bone, while permitting some motion of the wrist. The brace members can have a variable thickness, such as is shown in FIG. 20, which illustrates a thicker portion 344a of the bracing member 340 for providing additional rigidity. In some embodiments, an additional or different material may be added as a separate layer in addition to or in place of the thicker portion 344a.

The lower portion 344 portion may be rigid in the longitudinal plane and may be formed in any suitable shape to provide a desired stability to the wrist and/or arm.

In some embodiments, a material may be applied to portions of the wrist brace 10, 100, 200, 300 that face the wearer to stabilize the brace members on the skin and/or smooth features of the brace for comfort, such as a silicone (e.g., silicone caulking). The material applied to portions of the wrist brace that face the wearer can act to smooth or create a tacky or friction interface against the skin to hold the wrist brace in position. The material may also cover rough features of the brace, such as the stitching, for added comfort. Silicone pads or other cushioning materials may be used to cushion bones or other elements of the wrist.

The foregoing is illustrative of the present invention and is not to be construed as limiting thereof. Although exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

That which is claimed is:

1. A wrist brace for providing support to carpal bones within a wrist of a user, the wrist brace comprising an elongated strap sized and configured to encircle an entire circumference of the wrist; a first bracing member on the elongated strap and configured for positioning on a volar side of the wrist; and a second bracing member spaced apart from the first bracing member on the elongated strap and configured for positioning on a dorsal side of the wrist;
    wherein the first and second bracing members extend outward from the elongated strap and have a surface area that, together with the elongated strap, configured to support the carpal bones within the wrist; and wherein the elongated strap includes a curvilinear strap portion in use and is formed of a material that has a greater tensile stiffness along its length as compared to its width such that the elongated strap is compliant along its width to permit flexing of the wrist and has lesser flexibility along a length of the elongated strap to thereby stabilize bones of the wrist, and the elongated strap, including the curvilinear strap portion, has greater flexibility in a direction perpendicular to the circumference of the wrist configured in a proximal to distal direction, and the width of the elongated strap is between 0.5 cm and 3.0 cm and is sized and configured so as to overlie carpal bones without overlapping metacarpal bones, a radius and the ulna.

2. The wrist brace of claim 1, wherein the second bracing member comprises a compliant or rigid material or a preformed hyperbolic paraboloid.

3. The wrist brace of claim 1, wherein the first bracing member comprises a compliant curved or flat shape.

4. The wrist brace of claim 1, wherein a thickness of the first bracing member is uniform across its surface area or is greater in a central portion thereof as compared to a peripheral portion thereof.

5. The wrist brace of claim 1, wherein at least one of the first and second bracing members are slidably attached to the elongated strap so as to move with respect to another one of the first and second bracing members.

6. The wrist brace of claim 1, wherein a thickness of the second bracing member is greater in a central portion thereof as compared to a peripheral portion thereof.

7. The wrist brace of claim 1, wherein the first and second bracing members are formed of a polymeric material.

8. The wrist brace of claim 1, wherein the elongated strap in a use position is configured to be positioned approximately distal to a radius and ulna and approximately proximal to a plurality of metacarpals.

9. The wrist brace of claim 1, wherein the second bracing member has a length along the elongated strap of about 3 to 7 cm and a width of about 3 to 10 cm.

10. The wrist brace of claim 1, wherein the first bracing member has a length along the elongated strap of about 2 to 5 cm and a width of about 3 to 7 cm.

11. The wrist brace of claim 1, wherein the first bracing member is positioned on the elongated strap such that, in use, the first bracing member is configured to be located over at least one selected carpal bone for stabilization.

12. The wrist brace of claim 1, wherein the first bracing member comprises a top portion above a plane of the elongated strap that forms a curved extension and an extended lower portion that extends away from the hand proximally along an arm of the user and has a curved, rectangular shape and configured to be located, in use, over at least one selected carpal bone for stabilization.

13. The wrist brace of claim 1, wherein the elongated strap comprises a closing unit configured to adjustably close and constrain the elongated strap in use on or around a wrist.

14. The wrist brace of claim 1, wherein the first and second bracing members are configured to distribute pressure on surfaces thereof.

15. The wrist brace of claim 1, wherein the material of the elongated strap is configured to maintain a uniform circumference and not stretch along the length of the strap while having compliance along its width to permit flexing of the wrist.

16. The wrist brace of claim 1, wherein the first and second brace members are flexible such that a tensile stiffness of the first and second brace members changes from an edge region to a center region, with the edge region having a lesser tensile stiffness than the center portion.

17. The wrist brace of claim 1, wherein the elongated strap is configured to not stretch along the length of the elongated strap to form a fixed circumferential length around the wrist and thereby provide additional stability for the wrist.

18. A method for supporting carpal bones of a wrist, comprising the step of positioning a wrist brace circumferentially over and around the carpal bones of the wrist, wherein the wrist brace comprises: an elongated strap sized and configured to encircle an entire circumference of the wrist; a first bracing member on the elongated strap and configured for positioning on a volar side of the wrist; and a second bracing member spaced apart from the first bracing member on the elongated strap and configured for positioning on a dorsal side of the wrist; wherein the first and second bracing members extend outward from the elongated strap and have a surface area that, together with the elongated strap, is configured to support the carpal bones within the wrist; and wherein the elongated strap includes a curvilinear strap portion in use and is formed of a material that has a greater tensile stiffness along its length as compared to its width such that the elongated strap is compliant along its width to permit flexing of the wrist and has lesser flexibility along a length of the elongated strap to thereby stabilize the wrist, and the elongated strap, including the curvilinear strap portion, has greater flexibility in a direction perpendicular to the circumference of the wrist configured in a proximal to distal direction, and the width of the elongated strap is between 0.5 cm and 3.0 cm and is sized and configured so as to overlie carpal bones without overlapping metacarpal bones, a radius and the ulna.

19. The method of claim 18, wherein the step of positioning a brace over and around carpal bones of the wrist comprises positioning a brace approximately distal to the radius and ulna and approximately proximal to a plurality of metacarpals.

20. The method of claim 18, wherein the material of the elongated strap is configured to maintain a uniform circumference and not stretch along the length of the strap while having compliance along its width to permit flexing of the wrist.

21. The method of claim 18, wherein the first and second brace members are flexible such that a tensile stiffness of the first and second brace members changes from an edge region to a center region, with the edge region having a lesser tensile stiffness than the center portion.

22. The method of claim 18, wherein the elongated strap is configured to not stretch along the length of the elongated strap to form a fixed circumferential length around the wrist and thereby provide additional stability for the wrist.

23. A wrist brace for providing support to carpal bones within a wrist of a user, the wrist brace comprising an elongated strap sized and configured to encircle an entire circumference of the wrist; a first bracing member on the elongated strap and configured for positioning on a volar side of the wrist; and a second bracing member spaced apart from the first bracing member on the elongated strap and configured for positioning on a dorsal side of the wrist; wherein the first and second bracing members extend outward from the elongated strap and have a surface area that, together with the elongated strap, configured to support the carpal bones within the wrist; and wherein the elongated strap includes a curvilinear strap portion in use and is formed of a material that has a greater tensile stiffness along its length as compared to its width such that the elongated strap is compliant along its width to permit flexing of the wrist and has lesser flexibility along a length of the elongated strap to thereby stabilize bones of the wrist, and the elongated strap, including the curvilinear strap portion, has greater flexibility in a direction perpendicular to the circumference of the wrist configured in a proximal to distal direction, and the wrist brace is configured to contact the wrist continuously around the entire circumference of the wrist and thereby provide stability for the wrist.

24. The wrist brace of claim 23, wherein the width of the elongated strap is between 0.5 cm and 3.0 cm and is sized and configured so as to overlie carpal bones without overlapping metacarpal bones, a radius, and an ulna or only partially overlapping at least one of the metacarpal bones, the radius, and the ulna.

* * * * *